United States Patent [19]

Jones, Jr. et al.

[11] Patent Number: 5,059,510

[45] Date of Patent: Oct. 22, 1991

[54] MEDIA FOR OPTICAL INFORMATION STORAGE COMPRISING AN ORGANIC MACROCYCLIC CHROMOPHORE SUBSTITUTED WITH A FILM CONFERRING ORGANIC SUBSTITUENT

[75] Inventors: R. Sidney Jones, Jr., Randolph; David E. Nikles, Colonia, both of N.J.; Malcolm E. Kenney, Cleveland Heights, Ohio

[73] Assignee: Hoechst Celanese Corp., Somerville, N.J.

[21] Appl. No.: 396,962

[22] Filed: Aug. 22, 1989

Related U.S. Application Data

[63] Continuation of Ser. No. 913,457, Sep. 30, 1986, abandoned, which is a continuation of Ser. No. 698,210, Feb. 4, 1985, abandoned.

[51] Int. Cl.$^5$ ............... G03C 1/492; C09B 47/04
[52] U.S. Cl. .................. 430/270; 430/945; 430/944; 430/19; 430/321; 430/322; 430/338; 430/495; 430/961; 430/17; 346/135.1; 346/76 L; 540/128; 540/121; 540/139; 540/145
[58] Field of Search ............... 430/945, 944, 270, 19, 430/321, 322, 338, 495, 961, 17, 271; 346/135.1, 76 L; 540/128, 121, 139, 145

[56] References Cited

U.S. PATENT DOCUMENTS 3,775,423  11/1973  Lamure ............... 540/121

FOREIGN PATENT DOCUMENTS 59-45195  3/1984  Japan ............... 430/945

OTHER PUBLICATIONS

Schechtman, "Conducting Polymethallonaphthalocyaninas and Related Macrocyclic Compounds" Aug. 1983, Graduate Thesis, Aug. 1983, Case Western Reserve University.
Kuroiwa et al., "Reversible Read-Write . . . Media", *Japanese Journal of Applied Physics*, Part 1, vol. 22, No. 2, Feb. 1983, pp. 340–343.

Primary Examiner—Cynthia Hamilton
Attorney, Agent, or Firm—P. S. Kalyanaraman

[57]  ABSTRACT

Provided is an information recording medium, e.g., an optical recording medium, and a method for recording information thereon. The information layer of the recording medium comprises an organo macrocyclic chromophore containing a central hetero atom or two central hydrogen atoms or isotopes of hydrogen, e.g., a naphthalocyanine having silicon as the hetero atom, which chromophore is substituted with at least one substituent conferring film forming properties to the chromophore, e.g., a monomer or oligomeric substituent comprised of acid, amide or ester units. The information layer thereby offers excellent thermomechanical properties and exhibits excellent absorption properties all in a single component material. By utilizing a single component material, the problem of dye/polymer phase separation frequently encountered in dye/polymer mixtures is also overcome.

5 Claims, No Drawings

MEDIA FOR OPTICAL INFORMATION STORAGE COMPRISING AN ORGANIC MACROCYCLIC CHROMOPHORE SUBSTITUTED WITH A FILM CONFERRING ORGANIC SUBSTITUENT

This application is a continuation of application Ser. No. 913,457, filed Sept. 30, 1986, now abandoned, which is a continuation of Ser. No. 698,210, filed Feb. 4, 1985, now abandoned.

BACKGROUND OF THE INVENTION

1. Field of the Invention

This invention relates to a novel optical information recording medium and the recording of information thereon. More particularly, the present invention relates to an information recording medium, preferably in the form of a disk or in a tape format, suitable for use with optical recording and playback apparatus, with the information layer of the recording medium comprising a chromophore. In particular, the chromophore is substituted with an organic substituent conferring film forming properties.

2. Description of the Prior Art

Optical recording methods in which light from a laser is focused upon the surface of a recording medium with sufficient intensity to cause a detectable change in the physical characteristics of the surface material have been proposed. Among these methods is the establishment of an information pattern of pits. In such methods, the information representative pattern of pits may be formed in the surface of the recording medium by suitably controlling the intensity of the focused light in accordance with the information to be recorded while relative motion is established between the recording medium and the focused light spot.

For instance, in recent years, attention has been increasingy paid to the information recording method in which information is written in a thin film of metal or the like formed on a substrate by using a laser ray or beam. According to such a method, the information recording has been accomplished by forming holes or recesses in the metallic thin film under the action of an energy beam such as a laser ray. See, e.g., U.S. Pat. No. 4,238,803.

The recording medium, of course, is one of the key elements in any optical information storage system. The commercial viability of the recording medium depends upon such technical parameters as the sharpness in recording and playback of the information, i.e., a high signal to noise ratio. Dyes and pigments have accordingly been employed in information layers, often to enhance the sensitivity of the recording layers a the particular wavelength of the laser being used, which results in a much sharper recording and playback of the information.

For example, Spong U.S. Pat. No. 4,097,895, describes a recording medium which comprises a light reflecting material, such as aluminum or gold, coated with a dye-containing light absorbing layer, such as fluorescein, which is operative with an argon laser light source. The thickness of the light absorbing layer is chosen so that the structure has minimum reflectivity. An incident light beam then ablates, vaporizes or melts the dye-containing light absorbing layer, leaving a hole and exposing the light reflecting layer. After recording at the wavelength of the recording light, maximum contrast between the minimum reflectance of the light absorbing layer and the reflectance of the light reflecting layer exists.

Carlson U.S. Pat. No. 3,475,760, discloses a system for directly recording information in a thermoplastic film as a deformation by using a high energy laser scanning beam of small diameter. It is further disclosed that the sensitivity of the films for laser film deformation recording can be enhanced by the addition of pigments or dyes which exhibit a high absorption at the laser wavelength. Erasure of the film deformation is accomplished by recording over the information to be erased using a similar laser beam but with a much smaller scan line spacing, preferably so as to provide overlap of the scan lines.

Other U.S. patents which disclose the use of a light absorbing dye in the recording layer include U.S. Pat. Nos. 4,412,231 and 4,446,223. The former patent discloses using a mixture of dyes having different light absorbing wavelengths so that the resulting recording layer has a light absorptivity of 80% or more at all the wavelengths in the range of from 400-900 nm. The latter patent discloses an optical information recording element comprising a support coated with a layer of an amorphous composition, which composition comprises a binder and an oxoindolizine or oxoindolizinium dye.

In a paper entitled "Single Wavelength Optical Recording in Pure, Solvent Coated Infrared Dye Layers" by Gravesteijn, Steenbergen and van der Veen, experiments on the use of certain dyes for optical recording for digital and video applications at GaAlAs laser wavelengths are reported. The paper was presented at the Proceeding of the SPIE, "Optical Storage Media", volume 420, June 6–10, 1983. The specific dyes discussed in the paper are squarylium dyes and pentamethine dyes. It is further suggested in the paper that the solubility of the squarylium dyes in organic solvents can be greatly increased by the introduction of t-butyl groups into thiopyrylium end groups.

The use of dyes in conjunction with optical recording media comprising a styrene oligomer is disclosed in the article by Kuroiwa et al appearing in the *Japanese Journal of Applied Physics*, Vol. 22, No. 2, February, 1983, pp. 340–343. Among the dyes and pigments discussed as being useful is a copper phthalocyanine pigment. Phase separation and incompatibility between the dyes and oligomers were noted in the article as being problems in the use of dyes for optical information media.

Thus, while dyes or pigments have been employed in the information storage layers of optical recording media due to their excellent absorption properties, problems are encountered with regard to the application of the dyes or pigments as a stable layer. The addition of dyes to film-forming polymers due to limited solubility of the dye in the polymer and the tendency of the dye/polymer mixture to phase separate over time, as noted above, are severe problems which need to be overcome. The search for an improved information storage medium comprising a dye or pigment overcoming the aforementioned problems is continuously ongoing. What is desired is a recording layer material which of course exhibits a high extinction coefficient, but which also exhibits excellent film-forming properties to enhance its coating applicability, and good solubility in solvents for ease of manipulation. A recording medium which further eliminates the problem of phase separation over time would also be most desirable. Excellent stability with respect to thermal actinic and oxidative degradation is also a desirable feature.

Accordingly, it is a major object of the present invention to provide a novel and improved recording medium which comprises a chromophore in the information layer.

It is yet another object of the present invention to provide a novel optical recording medium which allows for ready application of the chromophore layer to form a stable information layer, while still exhibiting excellent absorption properties.

Still another object of the present invention is to provide a novel recording medium which contains a chromophore in the information layer, yet for which the problem of phase separation over time frequently encountered in dye/polymer mixtures is eliminated.

Yet another object of the present invention is to provide a one-component material for use in an information layer of an optical recording medium which exhibits excellent film-forming and thermomechanical properties, and excellent absorption properties.

These and other objects, as well as the scope, nature and utilization of the invention, will be apparent to those skilled in the art from the following description and the appended claims.

SUMMARY OF THE INVENTION

In accordance with the foregoing objectives, provided hereby is a medium for storage of optical information, i.e., information recorded and played back by optical means, which medium comprises an organo macrocyclic chromophore containing a central hetero atom or two hydrogen atoms or isotopes of hydrogen, which chromophore is substituted with at least one, but preferably more than one, moiety or substituent conferring film forming properties. It is preferred that the film conferring substituent be that of a monomer or an oligomer, most preferably comprising acid, amide or ester units. It is also preferred that the organo macrocyclic chromophore is an aza-annulene, e.g., naphthalocyanine, with silicon as the most preferred central hetero atom.

In a most preferred embodiment, the medium for storage of optical information is in the form of a disk.

In another embodiment of the present invention, there is provided a method of recording information in a thin film deposited on a relatively thick substrate by irradiating the film with a laser beam in accordance with said information to form pits in the film, the improvement which comprises said film being comprised of an organo macrocyclic chromophore containing a central hetero atom or two central hydrogen atoms or isotopes of hydrogen, which chromophore is substituted with at least one, but preferably more than one, substituent conferring film forming properties.

In another embodiment there is provided by the present invention a readable information medium comprising a relatively thick and thermally stable substrate having coated thereon a layer comprising an information track comprised of a succession of spaced pits, said layer being comprised of an organo macrocyclic chromophore containing a central hetero atom or two central hydrogen atoms or isotopes of hydrogen, which chromophore is substituted with at least one organic substituent conferring film-forming properties.

DETAILED DESCRIPTION OF THE PREFERRED EMBODIMENTS

The chromophore compound of which the information layer of the recording medium is comprised is an organo macrocyclic chromophore containing a central hetero atom or two hydrogen atoms or isotopes of hydrogen, which chromophore is substituted with at least one, but preferably more than one, organic substituent conferring firm-forming properties. For purposes of the present invention, the organic substituent can also include silicon.

It is the combination of the chromophore and its organic substituents from which the film-forming properties arise. Such a one-component material allows one to realize the excellent absorption properties of the chromophore, e.g., high extinction coefficient, while also realizing the benefits of the thermomechanical properties of a film-forming material as a result of the film forming properties arising from the combination of the chromophore with the organic substituent. As well, since a single component material is used, the problem of dye/polymer phase separation is avoided. The result is an information layer exhibiting an excellent combination of absorption and thermomechanical properties while allowing one to easily apply the material as a film.

The one-component material of the information layer thereby comprises two portions, i.e., the chromophore portion and the film conferring organic substituents to the chromophore. The chromophore portion, i.e., the primary absorbing portion, of the one-component material preferably comprises at least 25% by weight of the material. Functionally, of course, the lower limit of the amount of the chromophore portion is determined by the suitable optical absorption properties of the material as provided by the chromophore portion. The upper limit of the amount of chromophore portion suitable is determined by the desired thermomechanical properties exhibited by the material.

The film conferring organic substituent of the chromophore which confers the desired thermomechanical properties to the one-component material is preferably a monomer or an oligomer, i.e., having from 2–100 monomer units, depending upon the molecular weight of the monomers chosen. In general, any precursor to a film-forming material may be suitable. The most preferred organic substituents, however, are comprised of ether, acid, amide, sulfonamide, ester, acrylate, epoxy, urethane, or silicone units, or mixtures thereof. The most preferred substituents are comprised of acid, amide, or ester units. As noted above, for the purposes of the present invention, the organic substituent can also include silicon.

The film conferring organic substituents of the chromophore can be substituted at a central hetero atom or any of the aromatic rings of the chromophore. When the chromophore is substituted by the film conferring organic substituent at a central hetero atom, it is preferred that the hetero atom be Si, Ge, Sn, a transition metal, Al, Ga or In. When the chromophore is substituted by the film conferring organic substituent at an aromatic ring, it is preferred that the hetero atom is an element of Group IIa, IIIb or IVb of the Periodic Table (see, F. A. Cotton and G. Wilkinson, *Advanced Inorganic Chemistry*, 4th Edition, John Wiley and Sons, 1980), or a transition metal. In any event, it is preferred that the central hetero atom, when employed, is silicon, germanium or tin, with silicon being the most preferred central hetero atom.

When the chromophore comprises two central hydrogen atoms or isotopes of hydrogen, of course, no substitution is possible at the central position of the chromophore. The isotopes of hydrogen would include deuterium and tritium. Chromophores having central hydrogen atoms are manufactured by first making the compound but with a central metal atom which is easily displaced. The metal is then replaced with the hydrogen atoms (or its isotopes) as is well known in the art.

The number of substitutions of the chromophore can be any amount practicable, the determining factor being the ultimate performance of the one-component material as the recording layer in an optical recording medium. Generally, the number of substitutions is chosen so that the absorption maximum for the one-component material corresponds with the output wavelength of the laser used in the optical recording. The thermomechanical properties of the material should also allow data to be recorded on the recording layer by a focused laser beam operating above a threshold power value for writing data and at a useful data rate. The data can then be read by a focused, but lower power, laser beam that causes no detrimental change in the signal obtained from the recording layer. The excellent absorption characteristics of the recording layer material allow the data to be read by changes in reflectivity. The thermomechanical properties of the one-component material can also be controlled by the number (and type) of substitutions to allow laser addressed erasure of the data and to allow a film of the material to be cast by any technique known to those skilled in the art of coating. In general, therefore, the substituents of the chromophore are carefully designed so that the desired spectroscopic, thermomechanical and film-forming properties are combined into a one-component recording layer material.

The number of substituents that has generally been found to be most suitable for purposes of a recording layer are within the following guidelines, which can vary, however, depending upon the particular properties desired. When the chromophore is substituted with the film conferring organic substituent at a central hetero atom, the number of such substitutions is 1 or 2. When the chromophore is substituted with the film conferring organic substituent at an aromatic ring, the number of such substitutions is between 1 and about 16, with the most preferred number of substitutions being between about 4 and 8. A combination of the two types of substitutions can be had. No substitution at the central position is possible when hydrogen or its isotope occupies the central position.

The preferred organo macrocyclic chromophore for the purposes of the present invention is an aza-annulene containing a central hetero atom. The preferred aza-annulene dyes are phthalocyanines, naphthalocyanines or substituted porphyrins. The macrocyclic portion of the chromophore can also be substituted with various substituents selected to influence the absorption spectrum of the chromophore. The substituents may be chosen such that the absorption maximum of the chromophore closely corresponds to the wavelength of light used in the recording, erasing, and in most cases, the reading processes. These substituents can also contribute to the ability of the one-component material to be film forming.

The most preferred aza-annulenes are the naphthalocyanines having the following structural formula with any isomers thereof being contemplated for the purposes of the present invention:

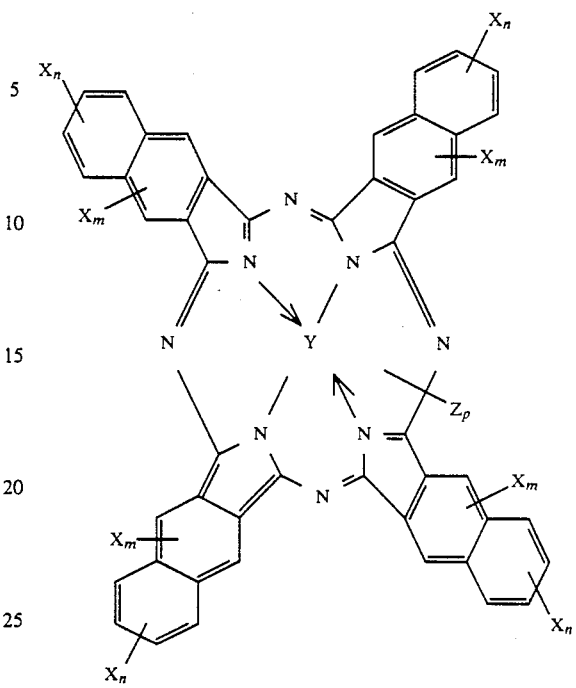

wherein the X substituents are independently selected organic substituents and can be the same or different, with n and m indicating the number of independently selected X substituents, each n being the same or different and ranging from 0 to 4, and each m being the same or different and ranging from 0 to 2. Z is also an organic substituent with p representing the number of Z substituents, with p being either 0, 1 or 2.

There must be at least one film conferring organic substituent. While only one type of film conferring substituent, X or Z, is generally required in a single molecular structure, both may be present. The method of chemically linking X and Z substituents to the dye ring or central atom can be any conventional method known to the skilled artisan.

More specifically, the Z substituents can be alike or different, and can be present to confer film forming and/or thermomechanical properties to the final one-component material. Similarly, the ring substituents X may be the same or different, with X being chosen to affect the absorption spectrum or the film forming and thermomechanical properties of the one-component material. A mixture of X substituents can also be chosen to affect both types of properties, i.e., spectral and thermomechanical.

The number of Z substituents is determined by the nature of the central heteroatom, Y. The coordination geometry of Y can be octahedral, square pyramidal, or square planar, depending upon Y being six, five, or four coordinate. When the coordination geometry is octahedral, two Z substituents are present. Examples of octahedral geometry would include Y being Si, Ge, Sn and certain transition metals, e.g., Ti, Zr, Hf. When the square pyramidal structure is present, only one Z substituent is attached to Y. Examples of this geometry include Al, Ga, and In. Square planar geometry results in no Z substituents. Examples include cases where Y is selected from group IIa of the Periodic Table and certain transition metals.

When Z substituents are present, film conferring and thermomechanical characteristics may arise from either the Z or X substituents. When Z substituents are absent, X substituents are used for this function In all cases, X substituents can be used to control the absorption spectrum of the material.

It is most preferred that Y is Si and that the film conferring substituents, whether the Z or X substituents, are comprised of acid, amide or ester units.

Examples of specific preferred one-component materials are materials of the following formula $SiNc(Z)_2$: where SiNc is silicon naphthalocyanine and Z is one of the following Scheme I

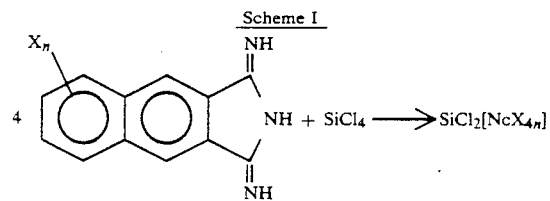

Scheme II

—$OSi(CH_3)_2O(CHCH_3CH_2O)_nH$, and n is approximately 7, 17 or 68;

—$OSi(CH_3)_2OCH_2CH_2CH_2NH(EMPOL-1010)NHCH_2CH_2CH_2OH$;

—$OSi(CH_3)_2OCH_2CH_2OCH_2CH_2NH(EMPOL-1010)NHCH_2CH_2OCH_2CH_2OH$;

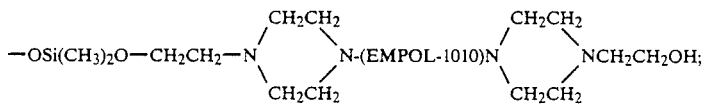

—$OSi(CH_3)_2O$—$CH_2CH_2CH_2NH(EMPOL-1010)NHCH_2CH_2NH(EMPOL-1010)NHCH_2CH_2CH_2OH$; and, —$OSi(CH_3)_2OCH_2CH_2OCH_2CH_2NH(EMPOL-1010)NHCH_2CH_2NH(EMPOL-1010)NHCH_2CH_2OCH_2CH_2OH$;

Scheme III

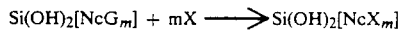

with Empol-1010 representing the residue of the corresponding dimer acid purchased from Emery Industries, Inc., Cincinnati, Ohio.

Such recording layer materials can be synthesized, for example, by the reaction of dihydroxysilicon naphthalocyanine with alcohol terminated monomers or oligomers through a dichlorodialkylsilane coupling agent. The synthesis of dihydroxysilicon naphthalocyanine is described in the doctoral dissertation of Lee Arnold Schechtman, "Conducting Poly(metallonaphthalocyanines) and Related Compounds", Case Western Reserve University, 1983. The polyether oligomers can be purchased from Aldrich Chemical Company and the degree of polymerization, n, can be estimated from the given average molecular weight. The alcohol-terminated dimer acid-amides can be prepared by the condensation of Empol-1010 (dimer acid purchased from Emery Industries, Inc. Cincinnati, Ohio) with the proper stoichiometry of the desired amino-alcohol and optionally the desired diamines. Direct reaction of dihydroxysilicon naphthalocyanine with the alcohol-terminated monomers or oligomers would also give acceptable materials. Reaction of dihydroxysilicon naphthalocyanine with a dichlorodialkylsilane coupling agent (dichlorodimethylsilane being most preferred) gives bis(chloro-dimethylsiloxy) silicon naphthalocyanine. This intermediate can be reacted with the alcohol terminated monomers or oligomers to give the desired product in good yield.

Ring substituted naphthalocyanine recording layer materials may be made by introducing the ring substituent X before adding the film conferring Z groups, if the Z groups are required to render the material film forming. The X ring substituent may be introduced in the naphthalocyanine precursor (scheme I below), by direct electrophilic aromatic substitution on the naphthalocyanine (scheme II below), or by nucleophilic aromatic substitution of a leaving group (G) on the naphthalocyanine ring (scheme III below).

Using Scheme I, one can introduce halogen, nitro, amino, amido (—NRCOR'), alkoxy, or mercapto groups Scheme II allows one to add sulfonate (—$SO_3^-$), sulfonamide ($SO_2NRR'$), halogen, alkyl, or acyl (—CO—) groups.

In Scheme III fluoro, chloro, or nitro groups, introduced by Scheme I, are displaced by nucleophiles, e g amino, alkoxy, or mercapto groups. Scheme I is preferred since it allows more control of the position and degree of ring substitution. Scheme II gives varying degrees of substitution and different geometrical isomers, such that the product is a complex mixture. Similarly, Scheme III gives various degrees of substitution and the reaction invariably results in a mixture of partially substituted starting material. In Scheme II and III, the original X group introduced may be modified to give the particular substitutent desired, e g., sulfonamides are produced by chlorosulfonating $Si(OH)_2Nc$, followed by treatment with amines. In any case, once the desired naphthalocyanine ring substitution is achieved, the Z groups may be attached with the chemistry used for $SiNc(OH)_2$.

The film formed by the one-component material of the present invention may be self-supporting, in which case any suitable or conventional casting technique may be used. Generally, however, it is preferred to cast the material as a film on a suitable support to add dimensional stability and support thereto. As well, the film may not always be self-supporting. The substrate may be optically featureless or may contain preformatting information (e.g., tracking groove and/or encoded information in the form of readable marks.) It is important when coating a substrate, of course, that an extremely flat homogeneous information recording surface be obtained to preclude the scattering of light.

Any suitable coating technique may be used to achieve such a flat surface, with a conventional technique such as spin coating, which allows for a high degree of control of film thickness and flatness, being preferred. It is, of course, important that the one-component material form a thin film coating.

The substrate which is coated should generally possess a surface of suitable smoothness. This may be imparted by appropriate molding or other forming techniques when the substrate is made. If the substrate has an inadequately smooth surface, a smoothing or subbing polymer layer may be used to attain the appropriate smoothness. Such a smoothing or subbing layer should not, of course, interfere with application or utilization of the recording layer which is subsequently applied thereto. The subbing layer can contain preformatting information.

A suitable protective layer or cover, such as those known to the art, can also be used if desired to protect the recording layer from dirt, dust, scratches or abrasion.

In an illustrative recording system embodying the principles of the present invention, a record blank disk form may be subject to rotation at a constant linear or constant angular velocity while a beam of light from a light source, e.g., a laser, is focused on the information surface of the disk. The intensity of the light beam is controlled in accordance with the information to be recorded. Illustratively, the control is effected in accordance with carrier waves modulated in frequency by information containing signals, with the light beam intensity varying as a result between a high level sufficient to effect a detectable change in the physical characteristics of the absorptive one-component recording layer material and a low level insufficient to effect such a detectable change, the frequency of the level alternations varying as the signal amplitude changes. Preferred writing speeds are in the range of from $10^6$ to $10^7$ bits per second.

The relative diameter and depth of the holes or pits formed will, of course, depend not only on the optical and thermal properties of the one-component information layer, but also on the characteristics of the writing beam, i.e., focused spot diameter, depth of focus, intensity profile and intensity and duration of the writing pulse. Optimization of these parameters is familiar to those skilled in the art.

As a result of the pit-formation in the one-component recording layer material, an information track comprising a succession of spaced pits is formed in the information surface of the disk, the pits appearing in those surface regions exposed to the high intensity beam. Variations in the length and separation of the pits are representative of the recorded information.

The result of the above-described recording process is the formation of an information record of a form which facilitates recovery of the recorded information by optical playback processes. The information track of such an information record comprises (1) undisturbed surface regions alternating with (2) pit regions formed by the pit-forming process, preferably coated on a substrate. This information track can be in either analog or digital form, for example, audio, video or computer data.

In playback or read operations pursuant to the principles of the present invention, a light beam is focused upon the information track of an information record. The playback beam has a constant intensity at a level insufficient to effect pit formation in the information layer or erasure of the recorded information by levelling. A photodetector, positioned to receive light reflected from the successive regions of the information track as they pass through the path of the focused light, develops a signal representative of the recorded information.

Several variations in the playback or reading system as known to the art are possible. The most preferred mode of reading information involves the relative reflection between the one-component material surface and those areas in which pits have been formed in the recordation of information. When the reflectivity of the one-component material surface is of relatively high reflectivity as compared to that of the substrate, the reflectivity in the areas of the pits will be less than in the regions without pits when a beam from the read laser passes thereby. Thus, a written bit can be registered as a decrease in reflected intensity. When the relative reflectivity of the one-component material surface is low as compared to that of the substrate, however, the reflectivity in the areas of the pits will be more than in the regions without pits when a beam from the read laser is focused thereon. Accordingly, a written bit can be registered as an increase in reflected intensity.

An advantage of the present invention is that the resulting information medium can also be suitable for erasure. Complete and accurate erasure of recorded information can be readily carried out by heating the medium to a sufficiently high temperature such that the one-component material becomes softened sufficiently to allow levelling of the surface. This can be done globally by heating the entire disk in an oven or some other suitable heating means, or by means of a defocused laser beam whose intensity at the surface of the information layer is intermediate between that of the write beam and read beam. It is generally necessary to heat an area greater than that of a single bit (typically 1 $\mu$m in diameter).

The present invention is further illustrated by the following examples, which pertain to the synthesis of various one-component materials useful as a recording layer in an optical recording medium. The details of the following examples, however, are in no way meant to be limitative, but rather merely illustrative.

EXAMPLE 1

Preparation of Bis(chlorodimethylsiloxy)silicon naphthalocyanine

To a dry 500 ml three necked round bottom boiling flask (equipped with magnetic stirring, a Dean-Stark moisture receiver, a reflux condenser, and a dry nitrogen purge) was added 300 ml dry pyridine (freshly distilled from calcium hydride), 2.0 g (2.58 mmol) dihydroxysilicon naphthalocyanine, and 20 ml tri-n-butylamine (dried over 4A molecular sieves). The mixture was heated to reflux and moisture was removed by azeotropic distillation until the water level (measured by Karl Fischer titration) was below 200 micrograms water per ml distillate. The reaction mixture was allowed to cool to room temperature and 8.0 ml (62 mmol) dichlorodimethylsilane was added via syringe. The mixture was allowed to stir at room temperature overnight ($\sim$18 hr). The next day, the excess dichlorodimethylsilane (b.p. 70°) was distilled from the reaction mixture. The distillation was continued until the boiling point of the distillate was greater than 115°, indicating that all dichlordimethylsilane was removed. This product was not isolated, but was immediately reacted with alcohol-terminated monomer or oligomer to make the desired product.

EXAMPLE 2

Preparation of Bis[hydroxy heptapropyleneoxydimethylsiloxy]silicon naphthalocyanine, i.e., SiNc-[OSi(CH$_3$)$_2$—O(CHCH$_3$CH$_2$O)$_7$H]$_2$ To the product mixture from the preparation of bis(-chlorodimethylsiloxy)silicon naphthalocyanine of Example 1, was added 2.19g (5.16 mmol) polypropylene glycol (425 average molecular weight). The stirred mixture was refluxed for 1 and ¾ hours under a blanket of dry nitrogen. The solution was allowed to cool to room temperature, suction filtered (no residue), and then stripped of its volatile components under vacuum. The resulting green oil was taken up in diethyl ether, extracted repeatedly with dilute HCl, and then washed repeatedly with water. The ether solution was dried over calcium sulfate and then the ether was stripped off under vacuum.

The product was a green solid with a melting point near 120° C. It was highly soluble in a number of organic solvents including dichloromethane.

EXAMPLE 3

Preparation of HOCH$_2$CH$_2$CH$_2$NH(EMPOL-1010)NHCH$_2$CH$_2$NH(EMPOL-1010)NHCH$_2$CH$_2$CH$_2$OH To a dry 500 ml three-necked round bottom blask equipped with mechanical stirring, a Dean-Stark moisture receiver, a reflux condenser, and dry nitrogen purge, was added 13.52 g (0.18 mol) 3-amino-l-propanol, 5.41 g (0.09 mol) 1,2-diaminoethane, and 102.24g (0.18 mol) Empol-1010. The stirring mixture was slowly heated to 250° C. over 2 hr under nitrogen and the water byproduct of this condensation reaction was collected in the moisture receiver. The reaction mixture was stirred for 2 hr at 250° C. under 1 atm N$_2$ and then heated at 250° C. another hour under reduced pressure (P<1 torr). The product was then allowed to cool to room temperature under nitrogen. This gave 113.56 g (99% yield) of a tacky, clear yellow solid with a broad melting range near 50° C. (determined by DSC).

EXAMPLE 4

Preparation of
SiNc[OSi(CH$_3$)$_2$OCH$_2$CH$_2$CH$_2$NH(Empol-1010)NHCH$_2$CH$_2$NH(Empol-1010)NHCH$_2$CH$_2$CH$_2$OH]$_2$ To the product solution from the preparation of bis(-chlorodimethylsiloxy)-silicon naphthalocyanine of Example 1, was added a solution of 7.24 g (5.68 mmol) alcohol-terminated monomer prepared in Example 3, in 35 ml dry pyridine. The mixture was refluxed for 2 hr and then allowed to cool to room temperature. The reaction mixture was poured into a mixture of 400 ml water and 200 ml ethanol to precipitate the green product. The product was isolated by suction filtration and then taken up in chloroform. The green chloroform solution was extracted repeatedly with dilute HCl and then washed repeatedly with water. The chloroform solution was filtered to remove any insolubles and then the solvent was removed under vacuum. The product was a deep green film-forming solid (yield 6.89 g).

EXAMPLE 5

Preparation of Dihydroxysilicon tetrachloronaphthalocyanine

Chloro-α,α,α',α',-tetrabromo-o-xylene

Bromine (7.6 ml) was added over a period of 4.5 hours to 4-chloro-o-xylene (5.0ml) at 120° C. in direct sunlight. The resultant product was cooled and the suspension formed was filtered by suction. The solid was washed with an ethanol-water solution (1:1) and then dried under vacuum overnight. The product is a white solid. Yield 16g, 92%.

6-Choro-2,3-naphthalenedicarbonitrile

A mixture of 4-chloro-α,α,α',α',-tetrabromo-o-xylene (4.83) fumaronitrile (1.109), sodium iodide (4.77 g) and dimethylformamide (35 ml) was stirred at 80° C. for 5.5 hours. The resulting mixture was cooled to near room temperature and then poured into water (500 ml). Enough NaHSO$_3$ (3.5 g) was added to the mixture to discharge the red color and render the mixture light tan. The solid was isolated from the suspension by suction filtration, washed with ether, and then dried under vacuum overnight. The product is a light tan solid. Yield 2.04g, 97%.

6-Chloro-1,3-diiminobenz(f)isoindoline

Anhydrous ammonia was bubbled through a stirred mixture of 6-chloro-2,3-naphthalenedicarbonitrile (2.08g), sodium methoxide (0.384 g), and methanol (100 ml) for 50 minutes. With continued ammonia addition, the mixture was refluxed for 3 hours. The solid was isolated from the suspension by suction filtration, washed with ether, and dried under vacuum overnight. The product is a light yellow solid. Yield 1.99 g, 83%.

Dichlorosilicon tetrachloronaphthalocyanine

6-Chloro-l,3-diiminobenz(f)isoindoline (1.88g) was added over a period of 15 minutes to a refluxing mixture of SiCl$_4$ (2.0 ml) and quinoline (50 ml). The resultant mixture was allowed to reflux for 45 minutes and then allowed to cool to room temperature. The suspension formed was filtered to isolate a green solid. The solid was washed with methanol, chloroform, pyridine and then dried under vacuum for 1 hour. Yield 1.17 g, 60%.

Dihydroxysilicon tetrachloronaphthalocyanine

A mixture of dichlorosilicon tetrachloronaphthalocyanine (1.07g) and concentrated sulfuric acid (40 ml) was stirred for 30 minutes. The brown mixture was poured onto ice (100 g) and the resulting suspension was filtered by suction. The brown solid was washed repeatedly with acetone and water (1:1). A mixture of the solid obtained and concentrated ammonia (30 ml) was refluxed for 1 hour. The green solid product was isolated by suction filtration, washed with water, then acetone, and dried under vacuum overnight. Yield 0.89 g, 87%.

EXAMPLE 6

Preparation of Sulfonamide Substituted Silicon Naphthalocyanines

A. Dihydroxysilicon polysulfonylchloride naphthalocyanine —Si(OH)$_2$[Nc(SO$_2$Cl)$_n$]

A mixture of dihydroxysilicon naphthalocyanine (0.4 g) and chlorosulfonic acid (1.3 ml) was stirred for 6 hours at 65° C. The resultant product was poured onto ice (100 g) which had been cooled with dry ice. The slurry was slowly warmed to melt the ice and then filtered. After washing with ice water, the solid was dried under vacuum overnight. Yield 0.66 g.

B. Dihydroxysilicon poly-N-di-n-octylsulfonamidonaphthalocyanine
—$Si(OH)_2[Nc(SO_2N((CH_2)_7CH_3)_2)_n]$ A mixture of the above product (0.50g) and di-n-octylamine (5.0 ml) was stirred at 63° C. for 2 hours. The product was isolated by suction filtration, washed with acetone, then water, and dried under vacuum overnight. The product is a deep green solid. Yield 0.62 g.

The degree of substitution, n, averages about 5 as indicated by material balance.

EXAMPLE 7

Preparation of Bis[hydroxyheptapropyleneoxydimethylsiloxy] silicon tetrachloronapthhthalocyanine —$Si[NcCl_4]$ $[OSi(CH_3)_2—O(CHCH_3CH_2O)_7H]_2$ To a dry 500 ml three necked round bottom flask (equipped with magnetic stirring, a Dean-Stark moisture receiver, a reflux condenser, and a dry nitrogen purge) is added 300 ml dry pyridine (freshly distilled from calcium hydride), 2.00 g (2.19 mmol) dihydroxysilicon tetrachloronaphthalocyanine, and 20 ml tri-n-butylamine (dried over 4A molecular sieves). The mixture is heated to reflux and moisture is removed by azeotropic distillation until the water level (measured by Karl Fischer titration) is below 200 micrograms water per ml distillate. The reaction mixture is allowed to cool to room temperature and 8.0 ml (62 mmol) dichlorodimethylsilane is added via syringe. The mixture is allowed to stir at room temperature overnight (about 18 hr). The next day, the excess dichlorodimethylsilane (b.p. 70° C.) is distilled from the reaction mixture. The distillation is continued until the boiling point of the distillate is greater than 115° C., indicating that all dichlorodimethylsilane is removed. To this reaction mixture is added 1.86 g(4.38 mmol) polypropylene glycol (425 average molecular weight). The stirring mixture is refluxed for 1.75 hours under a blanket of dry nitrogen. The solution is allowed to cool to room temperature, suction filtered (no solid residue), and then stripped of its volatile components under vacuum. The resulting green oil is taken up in diethyl ether, extracted repeatedly with dilute HCl, and then washed repeatedly with water. The ether solution is dried over calcium sulfate and then the ether is stripped off under vacuum. The product would be expected to be a green solid that is highly soluble in a number of organic solvents including dichloromethane.

The aforedescribed recording layer materials can be cast on substrates using a number of techniques known to those skilled in the art of coating (e.g., spin coating, roll coating). The materials have high solubility in one or more of the common solvents used for film casting (e.g., 1,2-dichloroethane, trichloroethylene, 1,1,2,2-tetrachloroethane, 2-butanone cyclohexanone, 1-butanol). They can be coated on a variety of substrate materials such as glass, aluminum, and polymeric materials (including polymethylmethacrylate and polycarbonate). They adhere well to the substrate material. Standard precautions known to those skilled in the art should be utilized to obtain films of acceptable quality for performance in optical recording media and the storage of information.

EXAMPLE 8

The product from Example 4 was spin coated from 1,1,2,2-tetrachloroethane solution onto glass substrates A 30 weight percent solution (3.0 g $SiNc[OSi(CH_3)_2OCH_2CH_2CH_2NH(EMPOL-1010)NHCH_2CH_2NH(Empol-1010)CHCH_2CH_2CH_2OH]$ and 7.0 g 1,1,2,2-tetrachloroethane) was carefully filtered through a 0.5 micrometer pore size membrane filter. The glass substrates were thoroughly cleaned by first treating with chromic acid solution, repeatedly rinsing with distilled water, and a final rinse with 1,1,2,2-tetrachloroethane. The substrates were dried under vacuum at 65° C. prior to coating. In the spin coating step the glass substrates were mounted on the spin coater and completely flooded with the green solution. The substrates were then spun at a rate (250 to 1000 rpm) that gave the desired film thickness for a time (20–60 sec) required for the film to reach steady state. The films were then baked in a vacuum oven at 65° C. overnight to remove 1,1,2,2-tetrachloroethane.

Although the invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. An optical information storage medium comprising an information recording layer which is a smooth, optical quality light absorptive layer in which changes can be induced and detected by using a laser focused upon the surface of the information layer, wherein the information recording layer comprises, as the major component of the information layer, an aza-annulene chromophore containing a central hetero atom wherein said hetero atom is substituted with a film conferring organic substituent, said substituent being a siloxy group containing an amide or ether function.

2. The optical information storage medium of claim 1, wherein the siloxy group is a di(lower alkyl)-monoalkoxysiloxy group containing the amide or ether function in the alkoxy moiety.

3. The optical information storage medium of claim 1, wherein the number of substituents at the central hetero atom is 2.

4. The optical information storage medium of claim 2, wherein the number of substituents at the central hetero atom is 2.

5. A method of forming a smooth, optical quality light absorptive information recording layer for storage of information, said method comprising the steps of:
   (i) dissolving, in a suitable solvent, an aza-annulene chromophore, containing a central hetero atom substituted with a siloxy substituent;
   (ii) coating said solution on a suitable substrate; and
   (iii) removing the solvent to leave behind a smooth film, the siloxy substituent conferring film-forming characteristics to the aza-annulene chromophore so that the information recording layer consists essentially of said chromophore.

* * * * *